United States Patent [19]
Arnett

[11] Patent Number: 5,725,503
[45] Date of Patent: Mar. 10, 1998

[54] RATCHETING NEEDLE PROTECTOR ASSEMBLY

[75] Inventor: Jeffery D. Arnett, Ypsilanti, Mich.

[73] Assignee: Aeroquip Corporation, Maumee, Ohio

[21] Appl. No.: 694,508

[22] Filed: Aug. 7, 1996

[51] Int. Cl.[6] .................................................. A61M 5/00
[52] U.S. Cl. ........................ 604/162; 604/165; 604/192
[58] Field of Search ................................. 604/263, 187, 604/192, 198, 110, 164, 165, 280, 162

[56] References Cited

U.S. PATENT DOCUMENTS

| | | | |
|---|---|---|---|
| 4,211,741 | 7/1980 | Ostoich | 264/173 |
| 4,254,773 | 3/1981 | Waldbillig | 128/348 |
| 4,391,029 | 7/1983 | Czuba et al. | 29/450 |
| 4,424,833 | 1/1984 | Spector et al. | 137/849 |
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,683,916 | 8/1987 | Raines | 137/854 |
| 4,713,057 | 12/1987 | Huttner et al. | 604/164 |
| 4,728,322 | 3/1988 | Walker et al. | 604/165 |
| 4,781,703 | 11/1988 | Walker et al. | 604/264 |
| 4,832,696 | 5/1989 | Luther et al. | 604/164 |
| 4,846,805 | 7/1989 | Sitar | 604/165 |
| 4,883,699 | 11/1989 | Aniuk et al. | 428/36.9 |
| 4,917,669 | 4/1990 | Bonaldo | 604/164 |
| 4,944,728 | 7/1990 | Carrell et al. | 604/164 |
| 4,952,207 | 8/1990 | Lemieux | 604/164 |
| 5,000,740 | 3/1991 | Ducharme et al. | 604/162 |
| 5,051,109 | 9/1991 | Simon | 604/263 |
| 5,088,985 | 2/1992 | Deras | 604/192 |
| 5,088,986 | 2/1992 | Nusbaum | 604/195 |
| 5,088,987 | 2/1992 | Noonan, Jr. | 604/195 |
| 5,088,988 | 2/1992 | Talonn et al. | 604/198 |
| 5,092,845 | 3/1992 | Chang | 604/164 |
| 5,092,853 | 3/1992 | Couvertier, II | 604/195 |
| 5,108,374 | 4/1992 | Lemieux | 604/164 |
| 5,127,905 | 7/1992 | Lemieux | 604/164 |
| 5,135,504 | 8/1992 | McLees | 604/164 |
| 5,171,230 | 12/1992 | Eland et al. | 604/250 |
| 5,183,469 | 2/1993 | Capaccio | 604/192 |
| 5,188,597 | 2/1993 | Sweeney et al. | 604/110 |
| 5,188,607 | 2/1993 | Wu | 604/167 |
| 5,201,713 | 4/1993 | Rosetti | 604/165 |
| 5,215,527 | 6/1993 | Beck et al. | 604/164 |
| 5,215,528 | 6/1993 | Purdy et al. | 604/164 |
| 5,226,899 | 7/1993 | Lee et al. | 604/282 |
| 5,234,416 | 8/1993 | Macaulay et al. | 604/282 |
| 5,240,537 | 8/1993 | Bodicky | 156/244.13 |
| 5,242,393 | 9/1993 | Brimhall et al. | 604/86 |
| 5,250,034 | 10/1993 | Appling et al. | 604/164 |
| 5,250,066 | 10/1993 | Lambert | 606/181 |
| 5,254,107 | 10/1993 | Soltesz | 604/282 |
| 5,261,885 | 11/1993 | Lui | 604/247 |
| 5,267,971 | 12/1993 | Brimhall | 604/177 |
| 5,267,979 | 12/1993 | Appling et al. | 604/247 |
| 5,273,543 | 12/1993 | Bell et al. | 604/110 |
| 5,279,591 | 1/1994 | Simon | 604/263 |
| 5,300,048 | 4/1994 | Drewes, Jr. et al. | 604/280 |
| 5,304,136 | 4/1994 | Erskine et al. | 604/110 |
| 5,304,140 | 4/1994 | Kugo et al. | 604/281 |
| 5,304,144 | 4/1994 | Brimhall | 604/177 |
| 5,304,149 | 4/1994 | Morigi | 604/192 |

(List continued on next page.)

*Primary Examiner*—John D. Yasko
*Attorney, Agent, or Firm*—Jones, Day, Reavis & Pogue

[57] ABSTRACT

A ratcheting needle protector assembly including a body, a needle hub and a needle. The body has a first end and a second end. The body defines a channel extending longitudinally between the first and second ends. The body defines receiving devices for receiving a pawl of a ratchet arm between the first and second ends. The needle hub has an external portion, an internal portion and a tracking member movably mounted on the body. The tracking member is positioned in the channel. The needle hub includes a ratchet arm having a pawl adapted to be received by the receiving devices. The needle is mounted on the internal portion of the needle hub. Movement of the needle hub from the first end to the second end of the body causes movement of the needle from outside the body to inside the body. The pawl of the ratchet arm is received by the receiving devices to prevent movement of the needle from inside the body.

11 Claims, 6 Drawing Sheets

U.S. PATENT DOCUMENTS

| | | | |
|---|---|---|---|
| 5,304,155 | 4/1994 | Lui | 604/247 |
| 5,306,253 | 4/1994 | Brimhall | 604/165 |
| 5,308,330 | 5/1994 | Grimard | 604/110 |
| 5,312,361 | 5/1994 | Zadini et al. | 604/165 |
| 5,312,371 | 5/1994 | Dombrowski et al. | 604/198 |
| 5,316,706 | 5/1994 | Muni et al. | 264/25 |
| 5,328,473 | 7/1994 | Fayngold et al. | 604/110 |
| 5,334,144 | 8/1994 | Alchas et al. | 604/68 |
| 5,338,310 | 8/1994 | Lewandowski | 604/192 |
| 5,342,309 | 8/1994 | Hausser | 604/110 |
| 5,344,404 | 9/1994 | Benson | 604/110 |
| 5,344,408 | 9/1994 | Partika | 604/192 |
| 5,356,390 | 10/1994 | Erskine | 604/164 |
| 5,370,624 | 12/1994 | Edwards et al. | 604/169 |
| 5,376,073 | 12/1994 | Graves et al. | 604/86 |
| 5,380,298 | 1/1995 | Zabetakis et al. | 604/265 |
| 5,380,307 | 1/1995 | Chee et al. | 604/264 |
| 5,385,554 | 1/1995 | Brimhall | 604/168 |
| 5,385,555 | 1/1995 | Hausser | 604/192 |
| 5,395,341 | 3/1995 | Slater | 604/164 |
| 5,397,512 | 3/1995 | Sloane, Jr. et al. | 264/25 |
| 5,405,323 | 4/1995 | Rogers et al. | 604/53 |
| 5,407,431 | 4/1995 | Botich et al. | 604/110 |
| 5,409,461 | 4/1995 | Steinman | 604/110 |
| 5,409,463 | 4/1995 | Thomas et al. | 604/167 |
| 5,409,644 | 4/1995 | Martin et al. | 264/25 |
| 5,411,486 | 5/1995 | Zadini et al. | 604/198 |
| 5,415,184 | 5/1995 | Peck | 128/880 |
| 5,417,668 | 5/1995 | Setzer et al. | 604/263 |
| 5,419,766 | 5/1995 | Chang et al. | 604/110 |
| 5,419,777 | 5/1995 | Hofling | 604/264 |
| 5,423,766 | 6/1995 | Di Cesare | 604/192 |
| 5,423,773 | 6/1995 | Jimenez | 604/282 |
| 5,425,712 | 6/1995 | Goodin | 604/96 |
| 5,425,735 | 6/1995 | Rosen et al. | 606/128 |
| 5,425,903 | 6/1995 | Sloane, Jr. et al. | 264/22 |
| 5,429,613 | 7/1995 | D'Amico | 604/198 |
| 5,429,617 | 7/1995 | Hammersmark et al. | 604/264 |
| 5,435,314 | 7/1995 | Dias | 128/662.06 |
| 5,437,648 | 8/1995 | Graves et al. | 604/263 |
| 5,441,489 | 8/1995 | Utsumi et al. | 604/280 |
| 5,443,457 | 8/1995 | Ginn et al. | 604/280 |
| 5,445,619 | 8/1995 | Burns | 604/192 |
| 5,445,624 | 8/1995 | Jimenez | 604/280 |
| 5,446,230 | 8/1995 | Travers et al. | 585/748 |
| 5,447,501 | 9/1995 | Karlsson et al. | 604/198 |
| 5,447,503 | 9/1995 | Miller | 604/280 |
| 5,447,724 | 9/1995 | Helmus et al. | 424/426 |
| 5,449,349 | 9/1995 | Sallee et al. | 604/180 |
| 5,453,095 | 9/1995 | Davila et al. | 604/167 |
| 5,453,099 | 9/1995 | Lee et al. | 604/282 |
| 5,456,668 | 10/1995 | Ogle, II | 604/110 |
| 5,456,674 | 10/1995 | Bos et al. | 604/280 |
| 5,458,658 | 10/1995 | Sircom | 604/192 |
| 5,462,533 | 10/1995 | Daugherty | 604/164 |
| 5,464,398 | 11/1995 | Haindl | 604/280 |
| 5,464,399 | 11/1995 | Boettger | 604/283 |
| 5,472,430 | 12/1995 | Vaillancourt et al. | 604/198 |
| 5,474,539 | 12/1995 | Costa et al. | 604/164 |
| 5,478,313 | 12/1995 | White | 604/110 |
| 5,478,328 | 12/1995 | Silverman et al. | 604/272 |

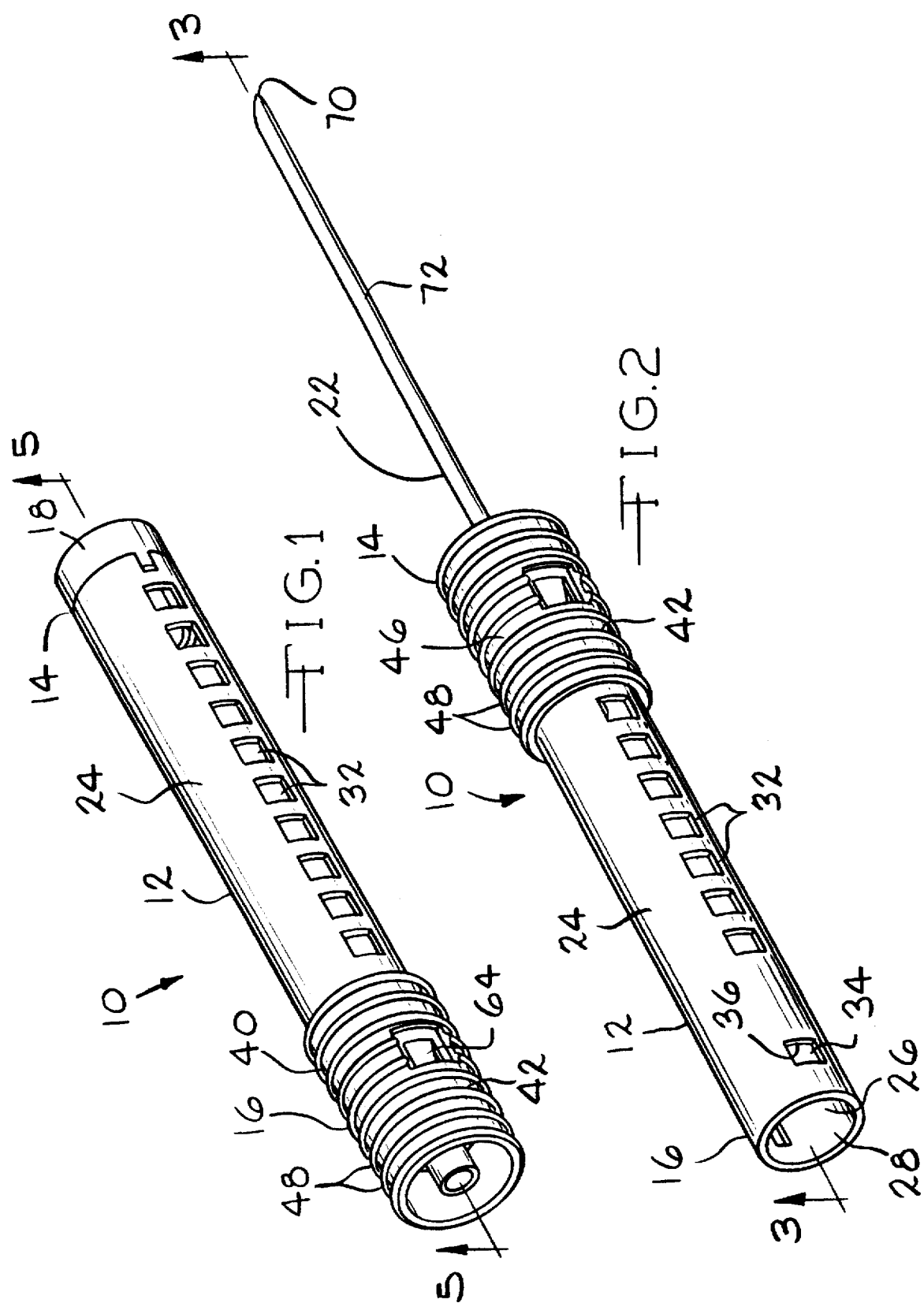

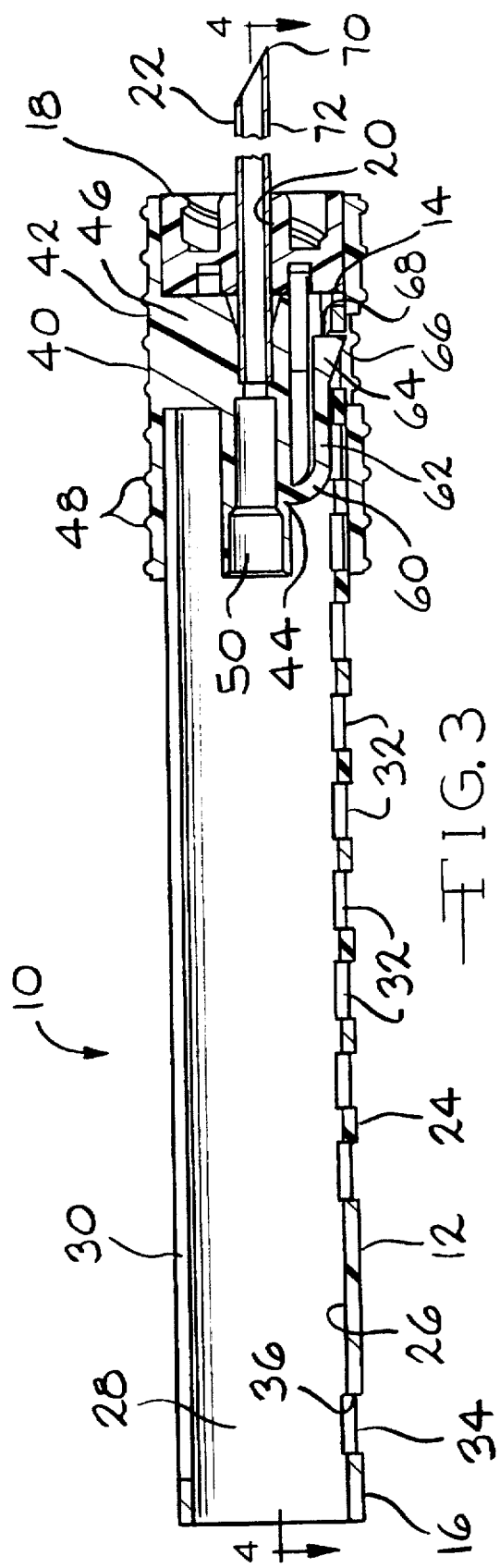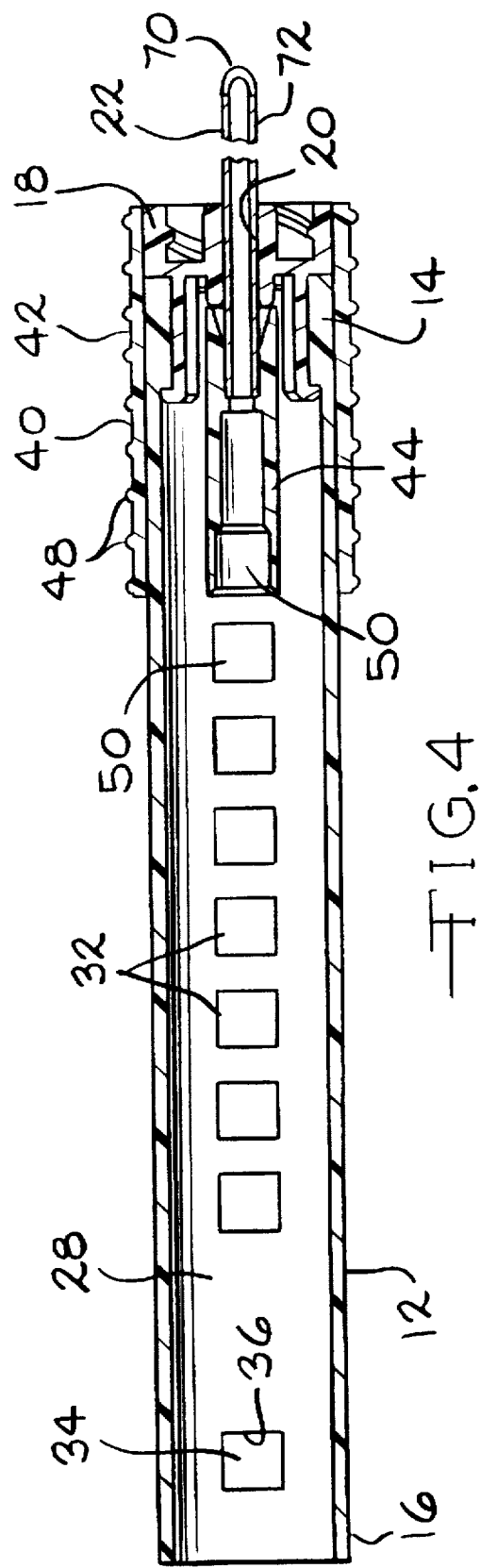

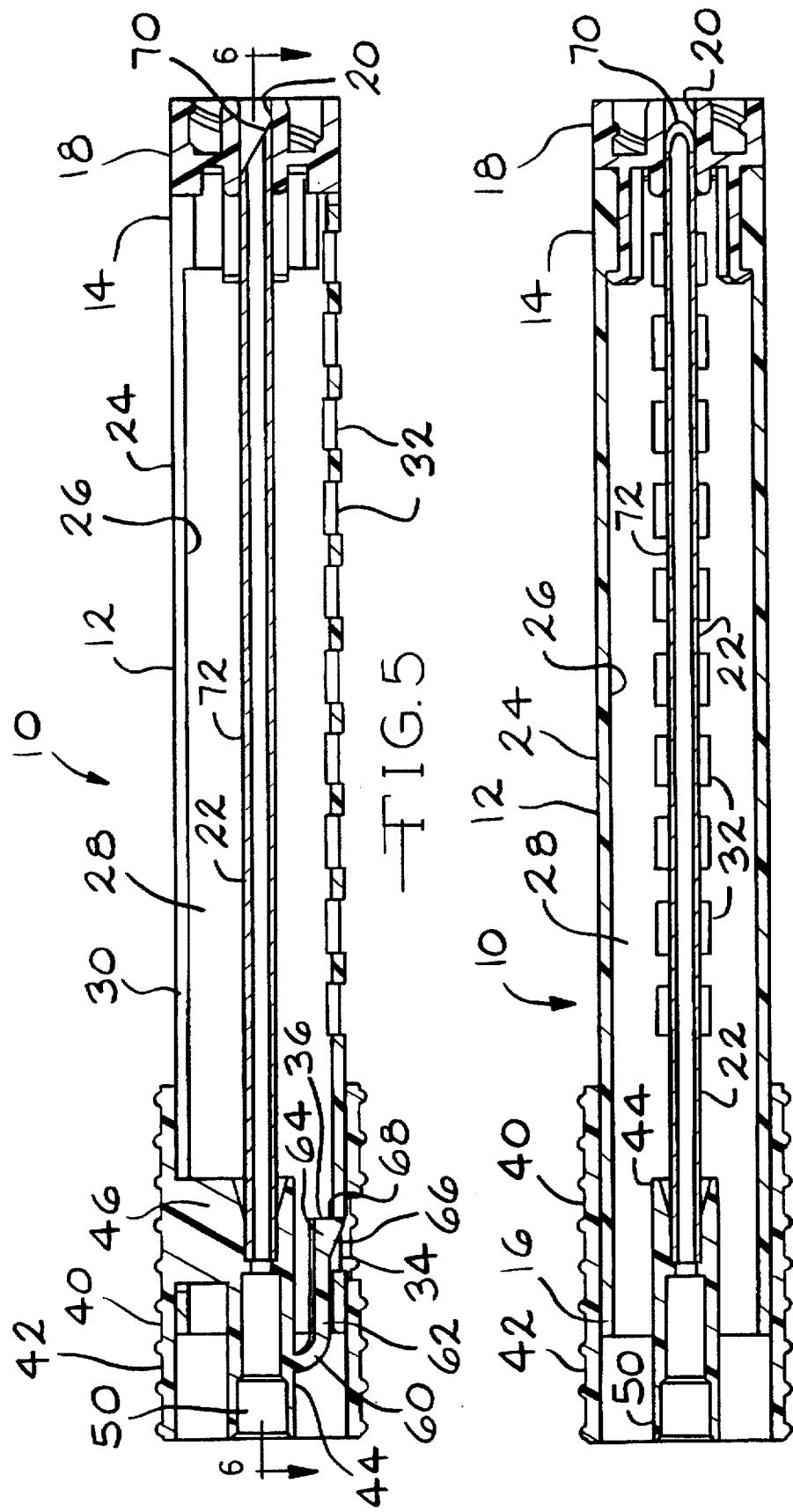

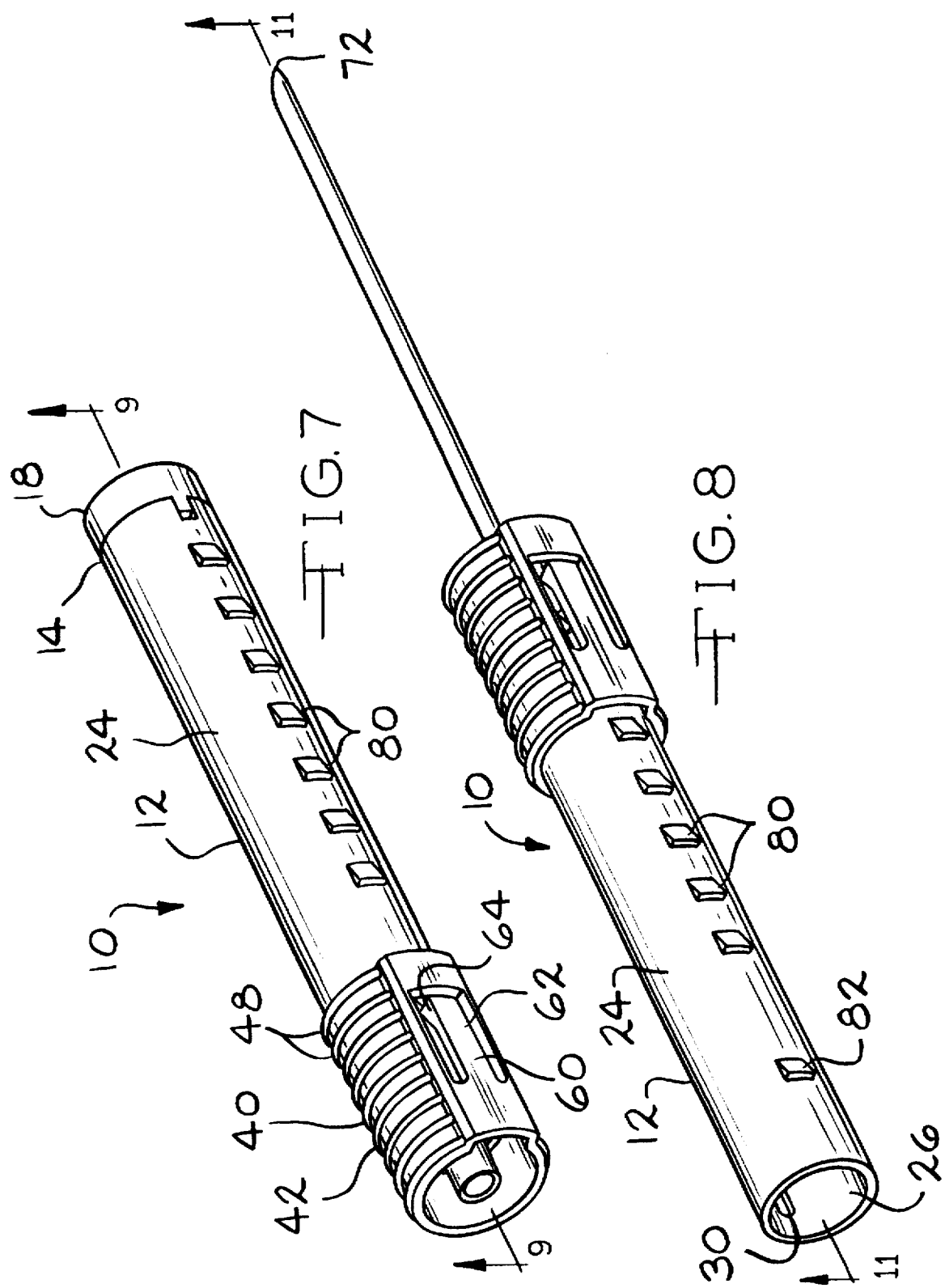

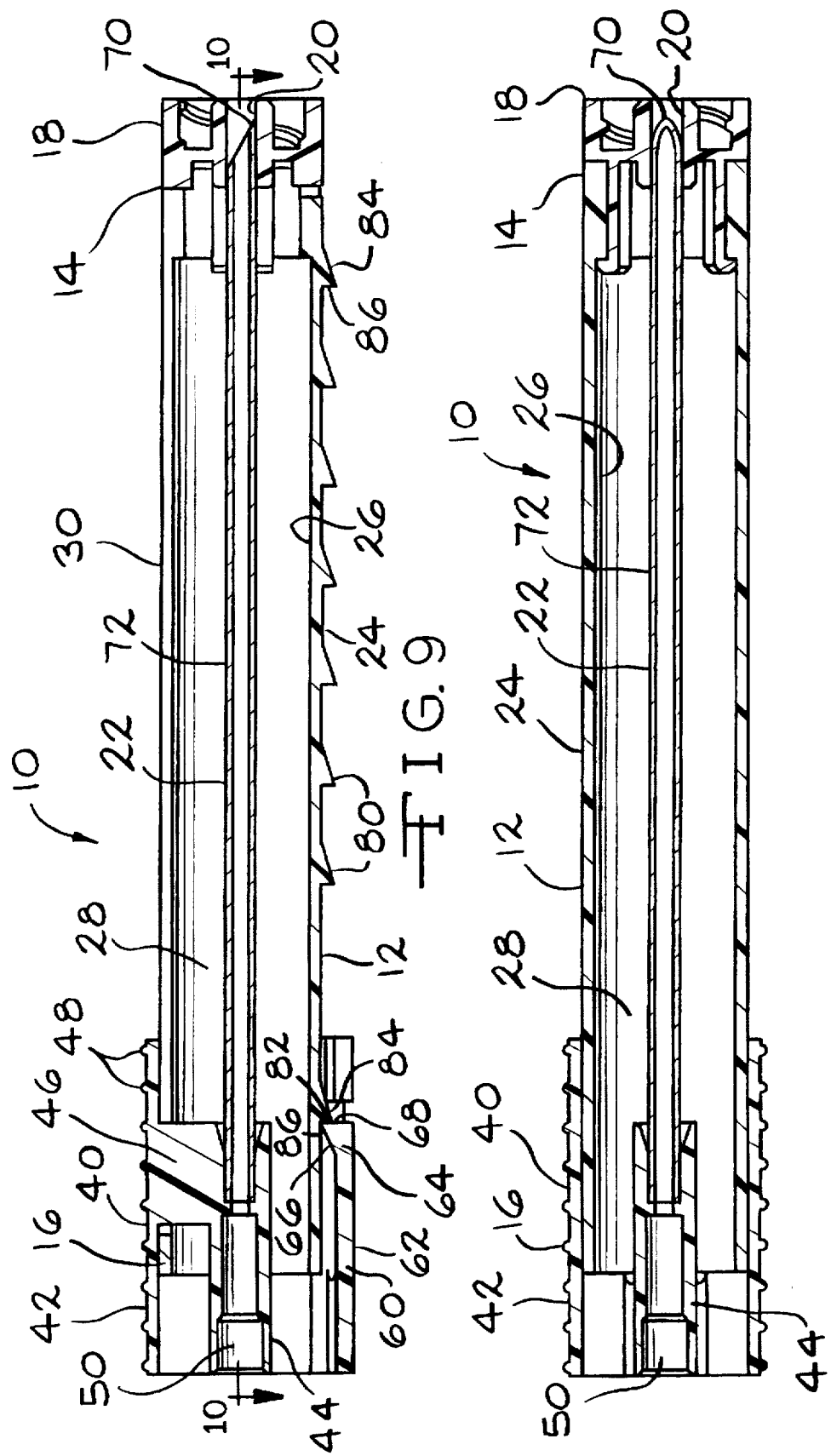

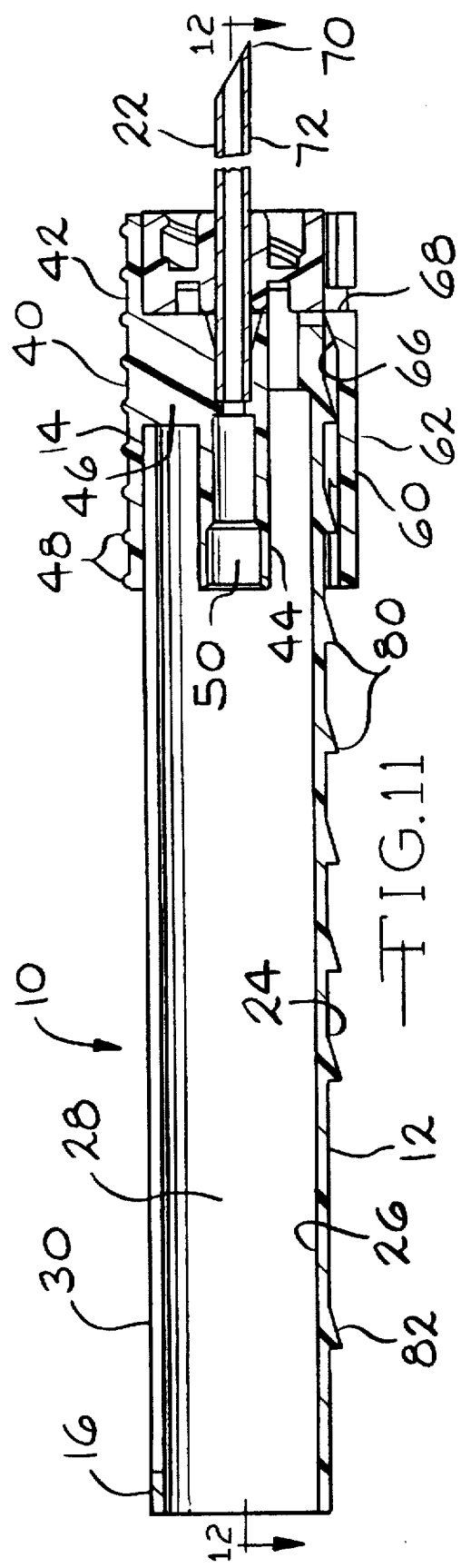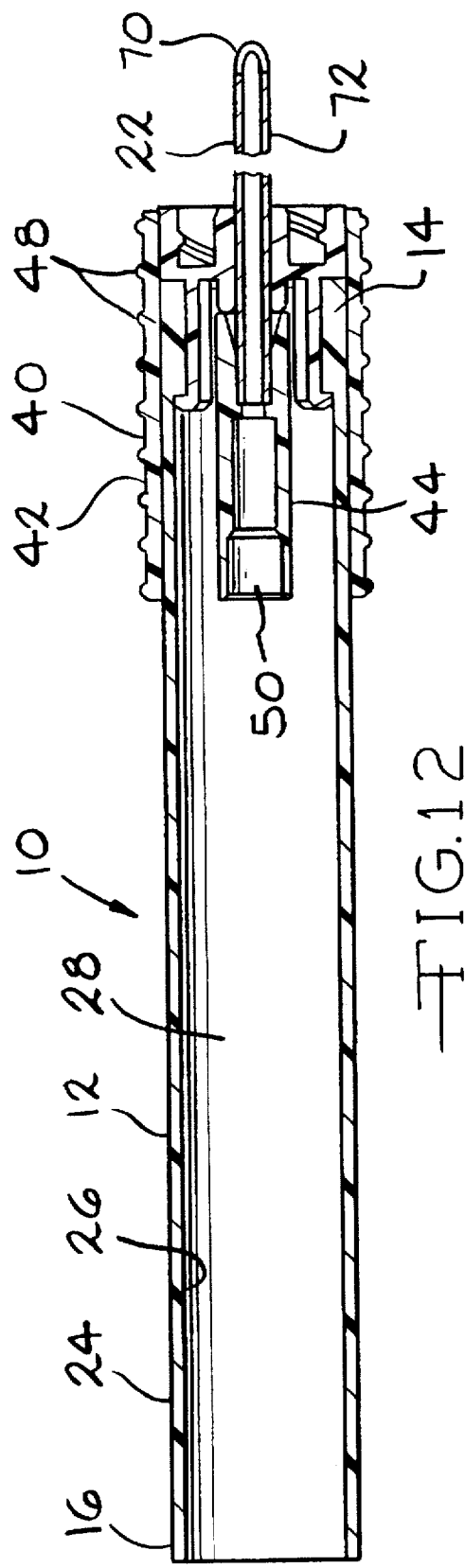

RATCHETING NEEDLE PROTECTOR ASSEMBLY

BACKGROUND OF THE INVENTION

The present invention relates to a needle protector. More specifically, the invention is directed to a ratcheting needle protector assembly having a body, a needle hub and a needle. The body defines receiving means for receiving a pawl of a ratchet arm that extends from the needle hub. The engagement of the pawl with the receiving means prevents backward movement of the needle and the needle hub to which the needle is attached.

It has been determined that certain viruses such as the hepatitis B virus can be transmitted from one person to another by accidental "needle-pokes". This type of accident can happen during medical procedures. An example of such a procedure is the insertion of a catheter into a blood vessel with a needle. After the catheter has been inserted in the blood vessel, the needle is removed from the cannula of the catheter at which time the pointed end of the needle can be accidentally poked into the person handling the needle or someone in the vicinity of the needle. Residual blood on the needle can be inserted in the person poked by the needle thereby transmitting a virus in the blood.

It has been found that there is a need for a ratcheting needle protector assembly in which the needle can be easily handled during insertion in a person and then retracted into the body of the needle protector so that the pointed end of the needle cannot come into contact with another person. The present invention satisfies this need.

SUMMARY OF THE INVENTION

The ratcheting needle protector assembly of the present invention includes a body, a needle hub and a needle. The body has a first end and a second end. The body defines a channel extending longitudinally between the first and second ends. The body defines receiving means for receiving a pawl of a ratchet arm between the first and second ends.

The needle hub has an external portion, an internal portion and a tracking member movably mounted on the body. The tracking member is positioned in the channel. The needle hub includes a ratchet arm having a pawl adapted to be received by the receiving means defined by the body.

A needle is movably mounted on the internal portion of the needle hub. The needle protector assembly is used, for example, to insert a cannula in a blood vessel. After insertion, the needle hub can be moved from the first end to the second end of the body. This causes movement of the needle from the outside of the body to the inside of the body. During movement, the pawl of the ratchet arm is received by the receiving means defined by the body. When the pawl is received by the receiving means, the needle hub and the needle are prevented from moving from the second end to the first end.

The primary object of the present invention is to provide a ratcheting needle protector assembly that receives a needle in the body of the assembly and prevents movement of the needle from the assembly.

Other objects and advantages of the present invention shall become apparent to those skilled in the art upon a review of the following detailed description of the preferred embodiments and the accompanying drawings.

BRIEF DESCRIPTION OF THE DRAWINGS

FIG. 1 is a perspective view of a first embodiment of the present invention with the needle hub positioned adjacent the second end of the body;

FIG. 2 is a perspective similar to the view of FIG. 1 in which the needle hub is positioned adjacent the first end of the body with the needle projecting outside the body;

FIG. 3 is a cross-sectional view taken through line 3—3 of FIG. 2;

FIG. 4 is a cross-sectional view taken through line 4—4 of FIG. 3;

FIG. 5 is a cross-sectional view taken through line 5—5 of FIG. 1;

FIG. 6 is a cross-sectional view taken through line 6—6 of FIG. 5;

FIG. 7 is a perspective view of a second embodiment of the present invention with the needle hub positioned adjacent the second end of the body;

FIG. 8 is a perspective view similar to the view of FIG. 7 with the needle hub positioned adjacent the first end of the body with the needle projecting outside the body;

FIG. 9 is a cross-sectional view taken through line 9—9 of FIG. 7;

FIG. 10 is a cross-sectional view taken through line 10—10 of FIG. 9;

FIG. 11 is a cross-sectional view taken through line 11—11 of FIG. 8; and

FIG. 12 is a cross-sectional view taken through line 12—12 of FIG. 11.

DETAILED DESCRIPTION OF THE PREFERRED EMBODIMENTS

The preferred embodiments and best mode of the present invention will now be described in detail with reference being made to the drawings. The ratcheting needle protector assembly according the present invention is indicated generally in the drawings by the reference number "10". The first embodiment assembly is shown in FIGS. 1–6. The second embodiment is shown in FIGS. 7–12.

Referring to FIGS. 2–4, the ratcheting needle protector assembly 10 includes a body 12 having a first end 14 and a second end 16. As shown in FIG. 3, the first end 14 is adapted to receive an end cap 18 that defines a needle opening 20 for receiving a needle 22.

As shown in FIG. 3, the body 12 consists of a hollow elongated cylinder having an exterior surface 24 and an interior surface 26. The interior surface 26 defines a cavity 28. The body 12 defines a channel 30 that extends longitudinally between the first and second ends 14 and 16.

Referring to FIGS. 2–4, the body 12 defines at least two spaced detents 32. In the present embodiment, the detents 32 are arranged in a row extending between the first and second ends 14 and 16. The detents 32 are positioned on the side of the body 12 opposite the channel 30. In the present embodiment, the body 12 defines eleven detents 32 extending between the first and second ends 14 and 16. It should be understood that the number of detents depends on the application of the assembly 10. The body 12 defines a locking detent 34 having a locking detent edge 36 adjacent the second end 16 of the body 12.

Still referring to FIGS. 2–4, the assembly 10 includes a needle hub 40 movably mounted on the body 12. As shown in FIG. 3, the needle hub 40 includes an external portion 42, an internal portion 44 and a tracking member 46 that extends between the external and internal portions. The tracking member 46 is positioned in the channel 30. The external portion 42 of the needle hub 40 includes a plurality of circumferencially extending gripping members 48. The gripping members 48 prevent slippage of a user's fingers during use and movement of the needle hub 40. The internal portion 44 of the needle hub 40 defines a chamber 50 for receiving fluid from the needle 22 that is mounted on the internal portion. The chamber 50 contains blood and other bodily fluids that flash when the needle 22 is inserted in the tissue of a person.

As shown in FIG. 3, the internal portion 44 of the needle hub 40 includes a single integral ratchet arm 60. The ratchet arm 60 consists of an elongated flexible member 62 that extends longitudinally from the internal portion 44 and an outwardly projecting pawl 64 having a chamfer 66 adjacent a locking edge 68. The pawl 64 is adapted to be received by the detents 32 and 34.

Referring to FIGS. 2-4, the needle 22 includes a pointed end 70 and a hollow shaft 72 that is in communication with the chamber 50 of the internal portion 44. The needle 22 is mounted on the internal portion 44. Therefore, movement of the internal portion 44 results in corresponding movement of the needle 22.

The use of the assembly 10 will now be described. Referring to FIGS. 1-6, a portion of the needle 22 is positioned outside the body 12 when the needle hub 40 is positioned adjacent the first end 14 of the body. When the needle 22 is to be retracted into the body 12, the person operating the assembly 10 grips the external portion 42 of the needle hub 40 and pulls the external portion from the first end 14 toward the second end 16 of the body. As shown in FIG. 3, the chamfer 66 of the pawl 64 is allowed to travel along the interior surface 26 of the body 12 and is received by the detents 32. The tracking member 46 of the needle hub 40 travels along the channel 30. This causes the needle 22 to enter the cavity 28 of the body 12. When the needle hub 40 is adjacent the second end 16, the pointed end 70 enters the needle opening 20 of the end cap 18 where it is fully contained. As shown in FIG. 5, when the needle hub 40 is adjacent the second end 16, the flexible member 62 of the ratchet arm 60 causes the pawl 64 to move outwardly into the locking detent 34. The locking edge 68 of the pawl 64 engages the locking detent edge 36 to prevent movement of the needle hub 40 and thus the needle 22 from the second end 16 to the first end 14. The assembly 10 can be discarded after retraction of the needle 22 into the body 12.

A second embodiment of the assembly 10 is shown in FIGS. 7-12. In this embodiment, the body 12 defines at least two spaced ramps 80 on the exterior surface 24. The ramps 80 extend longitudinally in a row between the first and second ends 14 and 16. A locking ramp 82 is defined adjacent the second end 16. In the present embodiment, the body 12 defines eight ramps 80. It should be understood that the number of ramps depends on the application for the assembly 10.

As shown in FIG. 9, each of the ramps 80 and 82 includes an inclined surface 84 and a locking surface 86. Referring to FIGS. 8 and 9, 5 the external portion 42 of the needle hub 40 includes a single integral ratchet arm 60. The ratchet arm 60 consists of an elongated flexible member 62 that extends longitudinally from the external portion 42 and an inwardly projecting pawl 64. The pawl 64 includes a chamfer 66 adjacent a locking edge 68. The pawl 64 is adapted to be received by the locking surfaces 86 of the ramps 80 and the locking ramp 82.

The use of the second embodiment assembly 10 will now be described. Referring to FIGS. 7-12, when the needle hub 40 is positioned adjacent the first end 14 of the body 12, a portion of the needle 22 is positioned outside the body. When the needle 22 is to be retracted into the body 12, the person operating the assembly 10 grips the external portion 42 of the needle hub 40 and pulls the external portion from the first end 14 toward the second end 16. As shown in FIGS. 9 and 11, the chamfer 66 of the pawl 64 travels along the exterior surface 24 of the body 12 and the inclined surfaces 84 of the ramps 80 and 82. The flexible member 62 of the ratchet arm 60 causes the pawl 64 to move inwardly so that the locking edge 68 of the pawl engages the locking surfaces 86 of the ramps 80 and 82. This engagement prevents movement of the needle hub 40 and thus the needle 22 from the second end 16 to the first end 14. As shown in FIG. 9, when the needle hub 40 is adjacent the second end 16, the flexible member 62 of the ratchet arm 60 causes the locking edge 68 of the pawl 64 to engage the locking surface 86 of the locking ramp 82. When the needle hub 40 is adjacent the second end 16, the pointed end 70 of the needle 22 enters the needle opening 20 where it is fully contained. The engagement of the locking edge 68 with the locking surface 86 of the locking ramp 82 prevents movement of the needle hub 40 and the needle 22 from the first end 14 to the second end 16 to thus maintain the full containment of the pointed end 70. After retraction of the needle 22 into the body 12, the assembly 10 can be discarded.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. A ratcheting needle protector assembly, comprising:
   a body having a first end and a second end, said body defining a channel extending longitudinally between said first and second ends, said body defining receiving means for receiving a pawl of a ratchet arm between said first and second ends;
   a needle hub having an external portion, an internal portion and a tracking member movably mounted on said body, said tracking member positioned in said channel, said needle hub including a ratchet arm having a pawl adapted to be received by said receiving means; and
   a needle mounted on said internal portion of said needle hub, whereby movement of said needle hub from said first end to said second end of said body causes movement of said needle from outside said body to inside said body, said pawl being received by said receiving means to prevent movement of said needle hub and said needle from said second end to said first end.

2. The invention of claim 1, wherein said body is a substantially hollow elongated cylinder.

3. The invention of claim 1, wherein said first end includes an end cap defining a needle opening for receiving a needle.

4. The invention of claim 1, wherein said receiving means consists of at least two spaced detents.

5. The invention of claim 4, wherein said ratchet arm is integral with said internal portion of said needle hub.

6. The invention of claim 1, wherein said receiving means consists of at least two spaced ramps.

7. The invention of claim 6, wherein said ratchet arm is integral with said external portion of said needle hub.

8. The invention of claim 1, wherein said external portion includes gripping means for gripping said needle hub during use.

9. The invention of claim 1, wherein said internal portion defines a chamber in communication with said needle for receiving fluid.

10. A ratcheting needle protector assembly, comprising:
- a substantially cylindrical body having an exterior surface, an interior surface, a first end and a second end, said body defining a channel extending longitudinally between said first and second ends, said body defining at least two detents on said interior surface between said first and second ends;
- a needle hub having an external portion, an internal portion and a tracking member movably mounted on said body, said tracking member positioned in said channel, said internal portion including a ratchet arm having a pawl adapted to be received by said detents; and
- a needle mounted on said internal portion of said needle hub, whereby movement of said needle hub from said first end to said second end of said body causes movement of said needle from outside said body to inside said body, said pawl being received by said detents to prevent movement of said needle hub and said needle from said second end to said first end.

11. A ratcheting needle protector assembly, comprising:
- a substantially cylindrical body having an exterior surface, an interior surface, a first end and a second end, said body defining a channel extending longitudinally between said first and second ends, said body defining at least two ramps on said exterior surface between said first and second ends;
- a needle hub having an external portion, an internal portion and a tracking member movably mounted on said body, said tracking member positioned in said channel, said external portion including a ratchet arm having a pawl adapted to be received by said ramps; and
- a needle mounted on said internal portion of said needle hub, whereby movement of said needle hub from said first end to said second end of said body causes movement of said needle from outside said body to inside said body, said pawl being received by said ramps to prevent movement of said needle hub and said needle from said second end to said first end.

* * * * *